US00PP14451P29

(12) United States Plant Patent
Uchneat

(10) Patent No.: US PP14,451 P2
(45) Date of Patent: Jan. 6, 2004

(54) IMPATIENS PLANT NAMED 'BALPIXBROS'

(50) Latin Name: *Impatiens walleriana*
Varietal Denomination: Balpixbros

(75) Inventor: Michael S. Uchneat, St. Charles, IL (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,468

(22) Filed: Mar. 27, 2002

(51) Int. Cl.[7] ..... A01H 5/00
(52) U.S. Cl. ..... Plt./317
(58) Field of Search ..... Plt./317

*Primary Examiner*—Anne Marie Grunberg
(74) *Attorney, Agent, or Firm*—Wood, Phillips, Katz, Clark & Mortimer

(57) ABSTRACT

A new and distinct Impatiens plant named 'Balpixbros', characterized by its small dark burgundy-rose flowers, compact growth habit and dark green leaves.

1 Drawing Sheet

Latin name of the genus and species of plant claimed: *Impatiens walleriana.*
Variety denomination: 'Balpixbros'.

BACKGROUND OF THE INVENTION

The present invention comprises a new and distinct Impatiens plant, botanically known as *Impatiens walleriana* and hereinafter referred to by the cultivar name 'Balpixbros'.

'Balpixbros' is a product of a planned breeding program with the objective of developing Impatiens cultivars with small flowers and compact growth habits.

The female or seed parent of 'Balpixbros', 'Red Chico' (unpatented), has a more compact growth habit than 'Balpixbros' and red flowers. The male or pollen parent of 'Balpixbros', proprietary Impatiens variety SD01033-2 (unpatented), has pink and white bicolor flowers. The new cultivar was discovered and selected as a single seedling within the progeny of the above stated cross during January 2000 in a controlled environment at Arroyo Grande, Calif. The new cultivar was designated initially BFP-561.

Asexual reproduction of the new cultivar has been carried out at Arroyo Grande, Calif. and West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits small dark burgundy-rose flowers;

(b) forms dark green foliage;

(c) exhibits a good basal branching character; and (d) exhibits a compact growth habit.

The new cultivar of the present invention can be compared to 'Fify Violet' (U.S. Plant Pat. No. 11,557). However, in side-by-side comparisons, plants of the new cultivar are more vigorous and the lower surface of the leaves of 'Balpixbros' are solid green whereas the lower surface of the leaves of 'Fify Violet' have grayed purple blotches. 'Balpixbros' can also be compared to its sibling 'Balpixred' (U.S. Plant Pat. No. 10/109,410). However in side-by-side comparisons, the flower color of 'Balpixbros' is different than that of 'Balpixred'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill., U.S.A.

DETAILED BOTANICAL DESCRIPTION

The cultivar 'Balpixbros' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 13, 2002. The readings were taken between 2:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double poly carbonate covered greenhouse under conditions comparable to those used in commercial practice. A soilless growth medium was utilized while temperatures of approximately 68° to 75° F. (20° to 24° C.) during the day and approximately 55° to 65° F. (13° to 18° C.) during the night and light levels of 4,000 to 6,000 footcandles were maintained.

Classification:
*Botanical.*—*Impatiens walleriana*, cultivar 'Balpixbros'.

Parentage:
*Female parent.*—Impatiens variety 'Red Chico'.
*Male parent.*—Proprietary Impatiens variety designated SD01033-2.

Propagation:

*Type cutting.*—Terminal tip.

*Time to initiate root.*—Approximately 7 to 10 days.

*Time to develop roots.*—Approximately 21 to 30 days.

*Root description.*—Fibrous, branching.

Plant description:

*Crop time.*—Approximately 4 to 6 weeks are required to produce a finished plant from rooted cuttings.

*Habit of growth.*—Compact with good basal branching. Pinching is not required.

*Form.*—Upright and mounded.

*Height of foliage.*—A mature plant, 12 weeks after the planting of a rooted cutting, commonly measures approximately 18.3 cm.

*Plant spread.*—Approximately 25.5 cm.

*Lateral branches.*—An average of 9.5 branches per plant, approximately 7.7 cm in length and 4 mm in diameter, glabrous and 146D in color. Internode length at the middle of the branch is approximately 8 mm.

*Foliage.*—Arrangement is alternate. Leaves are single, ovate with crenate, ciliate margin, acuminate apex, attenuate base and are at an acute angle to the stem. Upper and lower surfaces are glabrous. Leaf length is approximately 3.1 cm and width is approximately 1.7 cm. The upper surface of mature foliage is 147A and the lower surface is closest to 147B. Both upper and lower surfaces have pinnate venation. Venation of upper surface is 145D and the venation of the lower surface is 138A. The petiole length is approximately 2 cm, the diameter is approximately 2 mm and the color is closest to 145D.

Flowering description:

*Flowering habit.*—Freely flowering.

*Natural flowering season.*—Year round in greenhouse environment and from spring through fall in outdoor garden.

Flower description:

*Type.*—Single and persistent.

*Size.*—Diameter is approximately 2.4 cm.

*Aspect.*—Flat.

*Corolla.*—Five petals with entire, undulate margin and smooth texture. Upper petal length is approximately 1 cm and width at widest point is 1 cm. The upper petal has flat apex and flat base. Lower and lateral petals are fused at their base. Lower and lateral petal length is approximately 1.3 cm and width is approximately 8 mm. Lower petals have emarginate apex and attenuate base. Lateral petals have rounded apex and attenuate base. Color of upper surface of upper and lateral petals is closest to but darker than 67A. Color of lower surface is 67B. Color of upper surface of lower petals is close to but darker than 67A with spot of 155D at base. Color of lower surface of lower petals is 67B.

*Peduncle.*—Glabrous, at an acute angle to the stem, approximately 1.9 cm in length and 1 mm in diameter. Peduncle color is 146D.

*Flower bud.*—Oval, approximately 8 mm in length and 5 mm in diameter at first color. Color is 64A.

*Sepals.*—Three. The lateral sepals are lanceolate in shape with acuminate apex and are approximately 2 mm in length, 1 mm in width and 146C in color. Lower sepal is modified into a spur.

*Spur.*—Sharply curved, 2 cm in length and 145A with overlay of 67B.

*Reproductive organs.*—Five stamens, 3 mm in length. Anthers are fused around pistil and 67C. Pollen is sparse and 82B. Pistil length is 3 mm. Style length is <1 mm and color is 155D. Stigma length is <1 mm and color is 70A . Ovary length is 2 mm and color is 143A.

Seed production: Seed production has not been observed.

Disease resistance: Resistance to pathogens has not been observed.

Hardiness zone: 'Balpixbros' is hardy in zones nine (9) and highter.

I claim:

1. A new and distinct cultivar of Impatiens plant named 'Balpixbros' substantially as herein shown and described, which:

(a) exhibits small dark burgundy-rose flowers;

(b) dark green foliage;

(c) a compact growth habit; and (d) a good basal branching character.

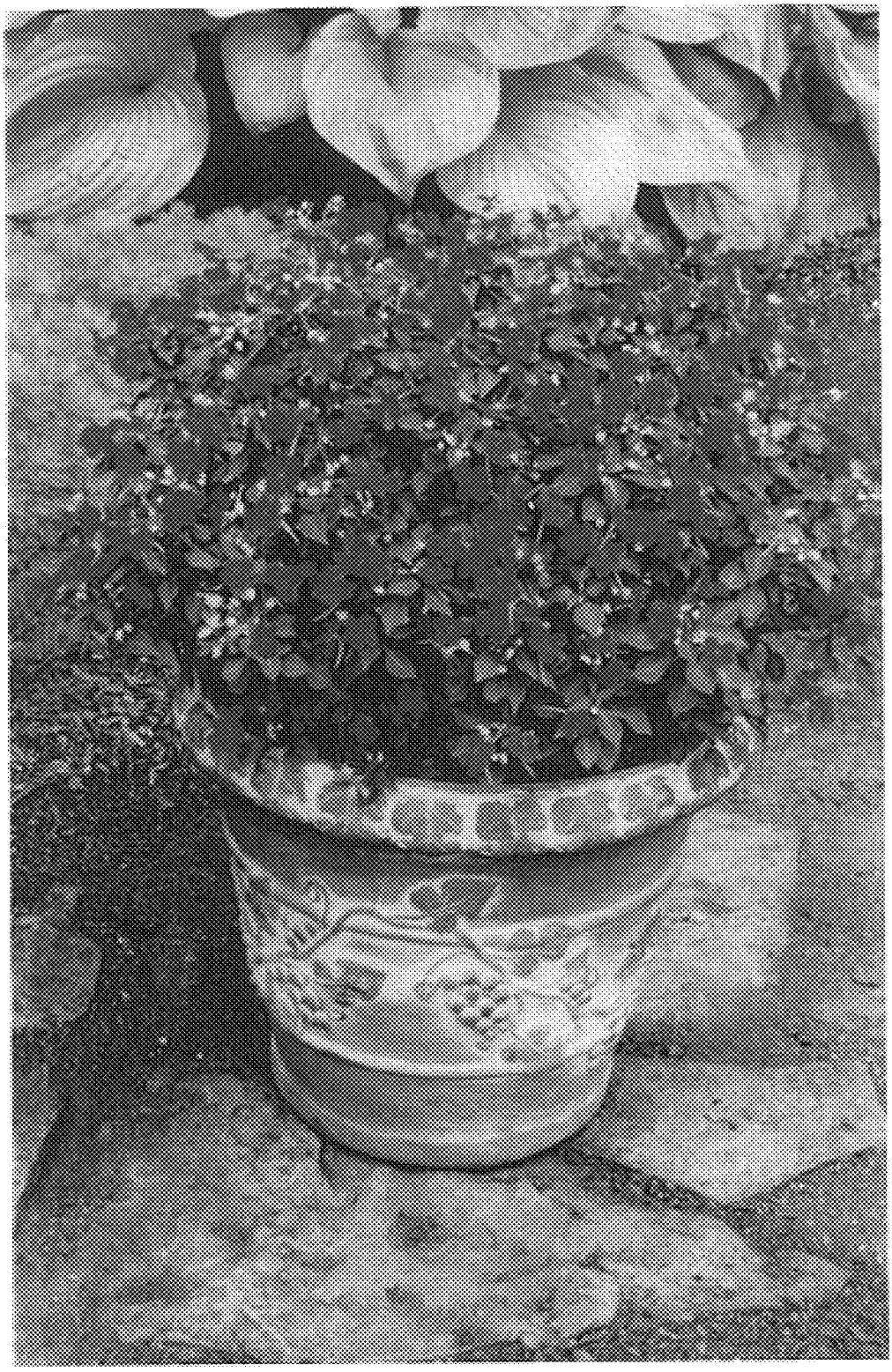

* * * * *